(12) United States Patent
Fukuda et al.

(10) Patent No.: US 7,248,905 B2
(45) Date of Patent: Jul. 24, 2007

(54) METHOD OF AND APPARATUS FOR MEASURING CONCENTRATION

(75) Inventors: Tadahiro Fukuda, Tokyo (JP); Takakazu Yano, Tokyo (JP); Kenji Matsumoto, Tokyo (JP)

(73) Assignee: Citizen Holdings Co., Ltd., Tokyo (JP)

( * ) Notice: Subject to any disclaimer, the term of this patent is extended or adjusted under 35 U.S.C. 154(b) by 640 days.

(21) Appl. No.: 10/448,107

(22) Filed: May 30, 2003

(65) Prior Publication Data
US 2004/0036854 A1 Feb. 26, 2004

(30) Foreign Application Priority Data
Jun. 17, 2002 (JP) ............................ 2002-175774
May 27, 2003 (JP) ............................ 2003-149021

(51) Int. Cl.
*A61B 5/00* (2006.01)

(52) U.S. Cl. ...................................... 600/310; 600/316
(58) Field of Classification Search ................ 600/310, 600/316, 318, 319, 322; 356/364, 366, 368
See application file for complete search history.

(56) References Cited

U.S. PATENT DOCUMENTS

| | | | | |
|---|---|---|---|---|
| 4,014,321 A | * | 3/1977 | March | 600/319 |
| 5,009,230 A | * | 4/1991 | Hutchinson | 600/316 |
| 5,209,231 A | * | 5/1993 | Cote et al. | 600/316 |
| 5,687,721 A | * | 11/1997 | Kuhls | 600/316 |
| 5,788,632 A | * | 8/1998 | Pezzaniti et al. | 600/316 |
| 5,956,144 A | * | 9/1999 | Kaplan et al. | 600/310 |
| 6,166,807 A | * | 12/2000 | Kawamura et al. | 600/316 |
| 6,246,893 B1 | * | 6/2001 | Gobeli | 600/319 |

FOREIGN PATENT DOCUMENTS

JP 2001-356089 A 12/2001

* cited by examiner

*Primary Examiner*—Eric F. Winakur
(74) *Attorney, Agent, or Firm*—Sughrue Mion, PLLC

(57) ABSTRACT

An optical rotation angle of linearly polarized light is modulated to obtain modulated light. The modulated light is passed through an inspection object containing an optically active substance. The optically active substance rotates an optical rotation angle of the modulated light. An intensity of light coming out of the inspection object is measured. Variation in the optical rotation angle of the modulated light is calculated based on the measured intensity and the angle to which the linearly polarized light is modulated. A concentration of the optically active substance in the pulsing component of the inspection object is calculated based on the variation in the optical rotation angle. Thus, concentration of glucose in the blood can be calculated without harming the patient.

18 Claims, 14 Drawing Sheets

METHOD OF AND APPARATUS FOR MEASURING CONCENTRATION

BACKGROUND OF THE INVENTION

1) Field of the Invention

The present invention relates to an apparatus for measuring a concentration of an optically active substance in an object to be inspected without causing any harm to the object. Particularly, the present invention relates to an apparatus for measuring the glucose concentration in the blood, that is, a blood sugar level.

2) Description of the Related Art

It is indispensable for a serious diabetic to grasp own blood sugar level. This is because of two major reasons. One, at present there is no complete remedial medicine for the diabetes. Second, the diabetic can control his own the blood sugar level only by taking a dose of insulin if there an increase in the blood sugar level, or by intake of glucose if there is a decrease in the blood sugar level.

Most of the methods currently employed for self-measurement of the blood sugar level harm (or attack) the patient, because, in most of these methods the blood is collected from the tip of the finger or arm with a syringe. Once the blood is collected, the blood sugar level is measured based on decomposition of the glucose contained in the blood using a glycolytic enzyme. These methods are quite accurate because the blood sugar level is measured directly from the blood. These methods will be referred to as "attacking methods".

Some patient may however need to measure blood sugar level a few times per day, for example, after every meal. If the attacking methods puncture the body of the patient, physical pains as well as mental anguish in blood collection may constitute a great burden to the patient. Further, the attacking methods are not suitable monitoring of the blood sugar level continuously. In other words, it is not possible to monitor the blood sugar level when the patient goes to sleep.

There are proposed methods of measuring the blood sugar level without collecting the blood. Since there is no need to collect the blood, these methods do not harm the patient. Some of these methods employ a body fluid such as sweat, and some measure urine sugar. Glucose amount such as in sweat or urine may however be incomplete in correlation with blood sugar level, and the measurement of blood sugar level may be inaccurate. These methods will be referred to as "non-attacking methods".

Many non-attacking methods proposed principally employ infrared rays of light. Among varieties of methods, some employ a light absorbing characteristic of glucose, and some, a back scattering characteristic of glucose.

A disclosed concentration measuring apparatus employs an optical rotatory tendency of glucose. As glucose has a tendency to optically rotate incident light, the concentration measuring apparatus is adapted to calculate a concentration of glucose by using an equation (1), such that:

$$\theta = \alpha CL \quad (1),$$

where $\theta$ is an optical rotation of light incident on glucose, $\alpha$ is an optical rotation coefficient of glucose, C is the concentration of glucose, and L is a length of optical path (see Japanese Patent Application Laid-Open Publication No. 2001-356089).

In reality, however, glucose concentration of blood in physical body is as low as from tens to hundreds mg/dl, in addition to the presence of various absorbing substances, scattering substances, etc. in blood, as well as in skin and other physical tissues. It is therefore very difficult to precisely measure glucose concentration in consideration such as of absorption and scattering of light. The blood sugar level generally indicates glucose concentration of blood, and even in the case using the optical rotation tendency, it is difficult to actually determine the length L of optical path across blood regions.

SUMMARY OF THE INVENTION

It is an object of the present invention to solve at least the problems in the conventional technology.

The concentration measuring apparatus according to one aspect of the present invention includes a linearly polarized light supplier that supplies linearly polarized light; an optical rotation angle modulator that modulates an optical rotation angle of the linearly polarized light to obtain modulated light; a light intensity detector that detects an intensity of light coming out of an inspection object when the modulated light is passed through the inspection object, wherein an optically active substance in the inspection object optically rotates the modulated light when the modulated light passes through the inspection object; a variation calculator that calculates a variation in the optical rotation angle of the light coming out of the inspection object based on an angle to which the optical rotation angle modulator has modulated the linearly polarized light and the intensity of the light detected by the light intensity detector, wherein the optical rotation angle of the light coming out of the inspection object varies in response to a pulsation of a pulsing component of the inspection object; and a concentration calculator that calculates a concentration of the optically active substance based on the variation in the optical rotation angle.

The concentration measuring method according to another aspect of the present invention includes supplying linearly polarized light; modulating an optical rotation angle of the linearly polarized light to obtain modulated light; passing the modulated light through an inspection object containing an optically active substance; detecting an intensity of light coming out of an inspection object, wherein the optically active substance in the inspection object optically rotates the modulated light when the modulated light passes through the inspection object; calculating a variation in the optical rotation angle of the light coming out of the inspection object based on the optical rotation angle to which the linearly polarized light was modulated and the intensity of the light detected, wherein the optical rotation angle of the light coming out of the inspection object varies in response to a pulsation of a pulsing component of the inspection object; and calculating a concentration of the optically active substance based on the variation in the optical rotation angle.

The other objects, features and advantages of the present invention are specifically set forth in or will become apparent from the following detailed descriptions of the invention when read in conjunction with the accompanying drawings.

DETAILED DESCRIPTION

Exemplary embodiments of the method and apparatus for measuring concentration according to the present invention will be explained below with reference to the accompanying drawings.

A method and an apparatus for measuring concentration according to a first embodiment of the present invention are explained below. The concentration measuring apparatus and the concentration measuring method are adapted to measure concentrations of optically active substances, such as glucose, plasma protein, or cholesterol, in an object. The object is, for example, blood, which is a pulsing component in the human body.

Figure 1:
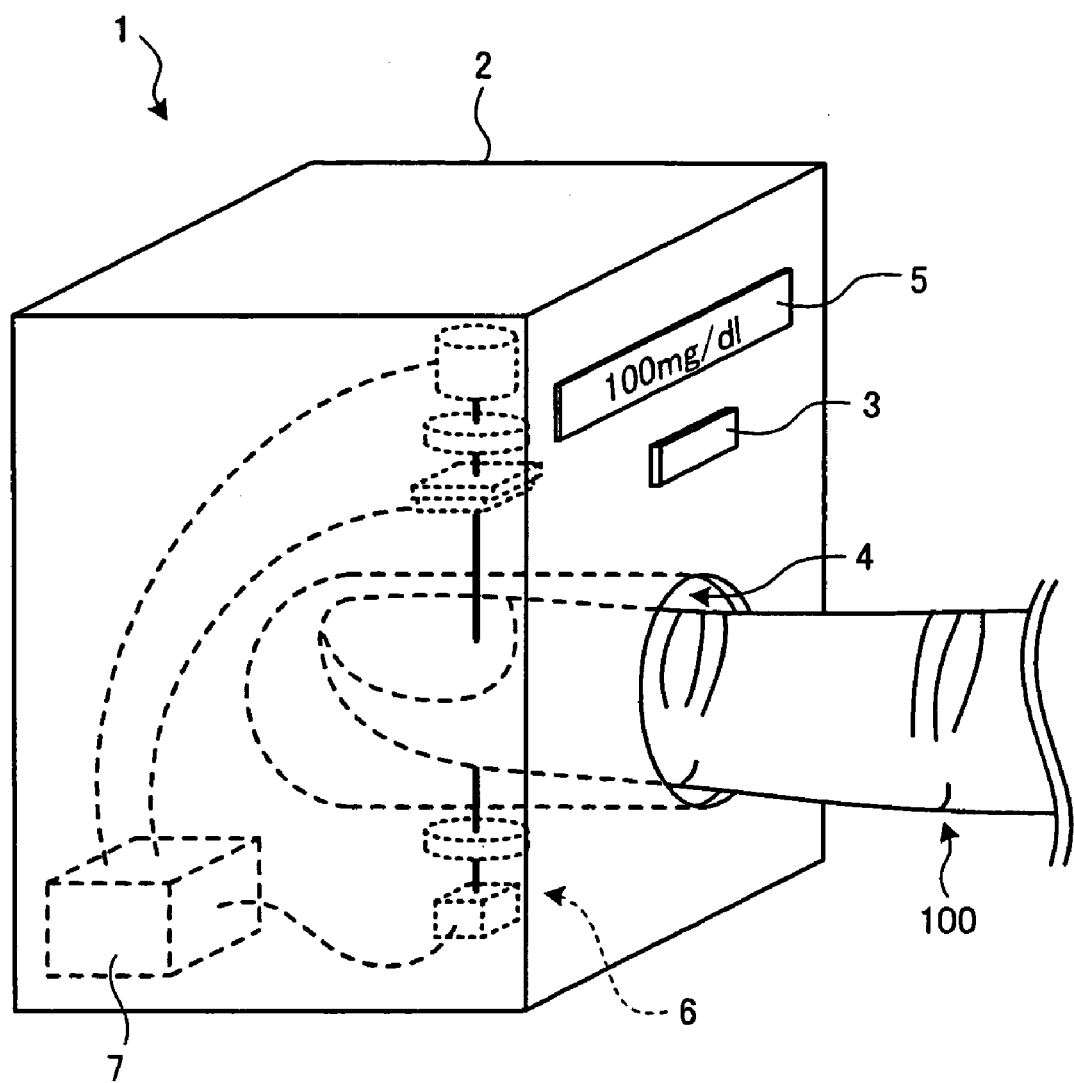
FIG. 1 is a schematic perspective view of a concentration measuring apparatus according to a first embodiment of the present invention.
Figure 2:
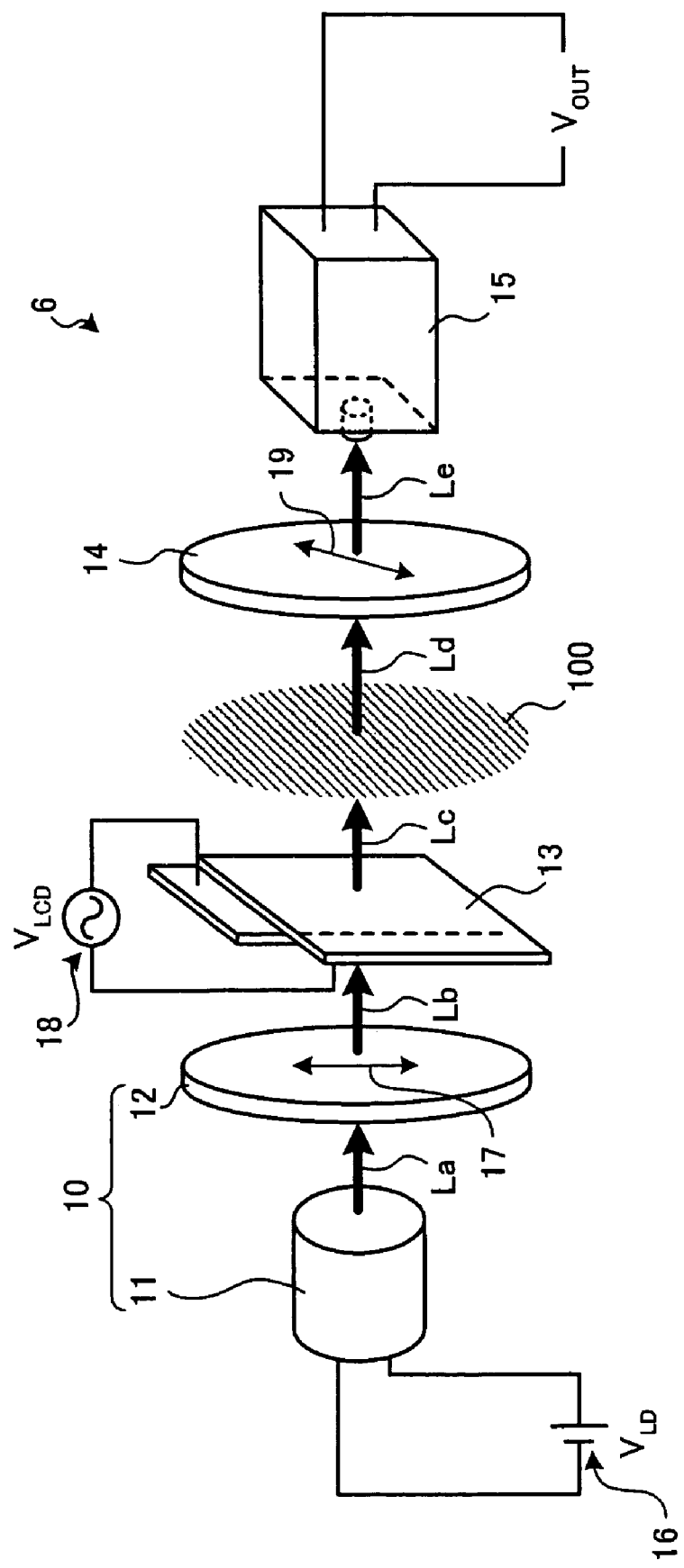
FIG. 2 is a schematic perspective view of a measuring system of the concentration measuring apparatus according to the first embodiment.

FIG. 1 shows, in a schematic perspective view, the concentration measuring apparatus 1 according to the first embodiment. FIG. 2 explains configuration of a measuring system 6 in the concentration measuring apparatus 1 according to the first embodiment. As shown in FIG. 1, the concentration measuring apparatus 1 includes a box-shaped body 2, an input section 3, an inspection object insertion hole 4, a liquid crystal display 5, the measuring system 6, and a control box 7. The input section 3, inspection object insertion hole 4, and liquid crystal display 5 are all provided at one side of the box-shaped body 2.

The inspection object insertion hole 4 admits insertion of an inspection object 100. The inspection object 100 is a part of the human body with relatively high light permeability. Examples of the inspection object 100 are the tip of the finger or the lobe of the ear. The liquid crystal display 5 displays concentrations of optically active substances contained in a pulsing component of the inspection object 100. As described later, a controller 20 calculates these concentrations.

As shown in FIGS. 1 and 2, the measuring system 6 includes a linearly polarized light output section 10 including a light source 11 and a first polarizer 12, an optical rotation angle modulator 13, a second polarizer 14, and a light intensity detector 15. The light source 11 includes a laser diode, a drive circuit, and an oscillator, for example.

The drive circuit achieves a frequency modulation or coding modulation of the laser diode. The oscillator outputs a clock signal to the drive circuit. When an instruction to start the measurement is output from the input section 3, a dc power supply 16 starts supplying power to the light source 11. As a result, the light source 11 projects a laser beam La of a predetermined wavelength to the first polarizer 12.

The first polarizer 12 has a polarization axis 17 in a Y-axis direction, and converts light of the laser beam La projected from the light source 11 into linearly polarized light Lb to be emitted to the optical rotation angle modulator 13. The linearly polarized light Lb has an optical axis in the axial direction of polarization axis 17. Linear-polarized light Lb output from the linearly polarized light output section 10 undergoes a modulation of optical rotation angle at the optical rotation angle modulator 13, to be emitted to the inspection object 100. As the optical rotation angle modulator 13, there is employed a TN liquid crystal cell, for example.

The TN liquid crystal cell 13 is connected to an ac power supply 18, and has an ac voltage applied therefrom. Linear-polarized light Lb past the first polarizer 12 is incident on the TN liquid crystal modulator 13, where the incident light Lb is optically rotated at a predetermined angle relative to its optical axis, to be emitted as polarized light Lc to the inspection object 100. The polarized light Lc, which is linear- or elliptically polarized, has its optical axis or major axis in a direction depending on the ac voltage applied from the ac power supply 18.

In a state with, for example, no ac voltage applied to the TN liquid crystal cell 13, the polarized light Lc to be emitted from the TN liquid crystal cell 13 has an optical (or major) axis optically levo-rotated at 90 degrees relative to the traveling direction of polarized light Lc. In a state with a sufficiently high ac voltage applied, the optical (or major) axis of the polarized light Lc to be emitted from the TN liquid crystal cell 13 is not optically rotated.

The second polarizer 14 has a polarization axis 19 crossing the polarization axis 17 of the first polarizer 12 at a predetermined angle. On the second polarizer 14 is incident polarized light Ld transmitted through the inspection object 100. The second polarizer 14 emits polarized light Le with an optical axis or major axis in the axial direction of its polarization axis 19.

The light intensity detector 15 receives polarized light Le transmitted through the second polarizer 14. The light intensity detector 15 is configured as a device independent of the optical rotation angle of incident polarized light Le, for a photoelectric conversion of the incident light Le to provide an output (detection voltage $V_{OUT}$) in proportion to an intensity of the incident light Le. The output from the light intensity detector 15 increases, as an angular difference between the optical axis of polarized light Ld transmitted through the inspection object 100 and the polarization axis 19 of the second polarizer 14 is nearer to 0 degree, and decreases, as the angular difference is nearer to 90 degrees.

The light intensity detector 15 may be configured, for example, with reverse-biased silicon-semiconductor PN junctions, photosensitive transistors, and light transmitting CdS devices. The light intensity detector 15 is adapted to detect whether an inspection object 100 is inserted in the inspection object insertion hole 4, from variation in intensity of the light to be detected.

Figure 3:
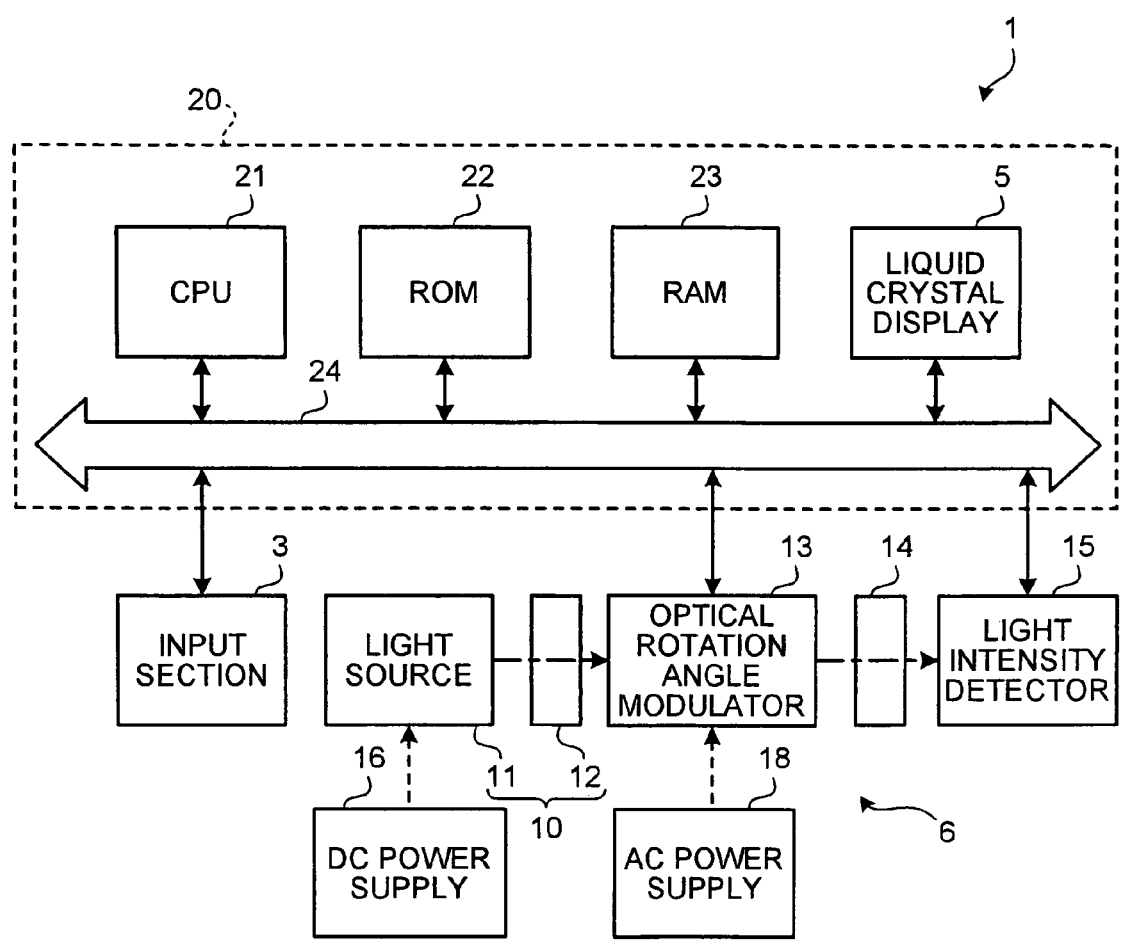
FIG. 3 is a block diagram of a hardware configuration of the concentration measuring apparatus according to the first embodiment.
Figure 4:
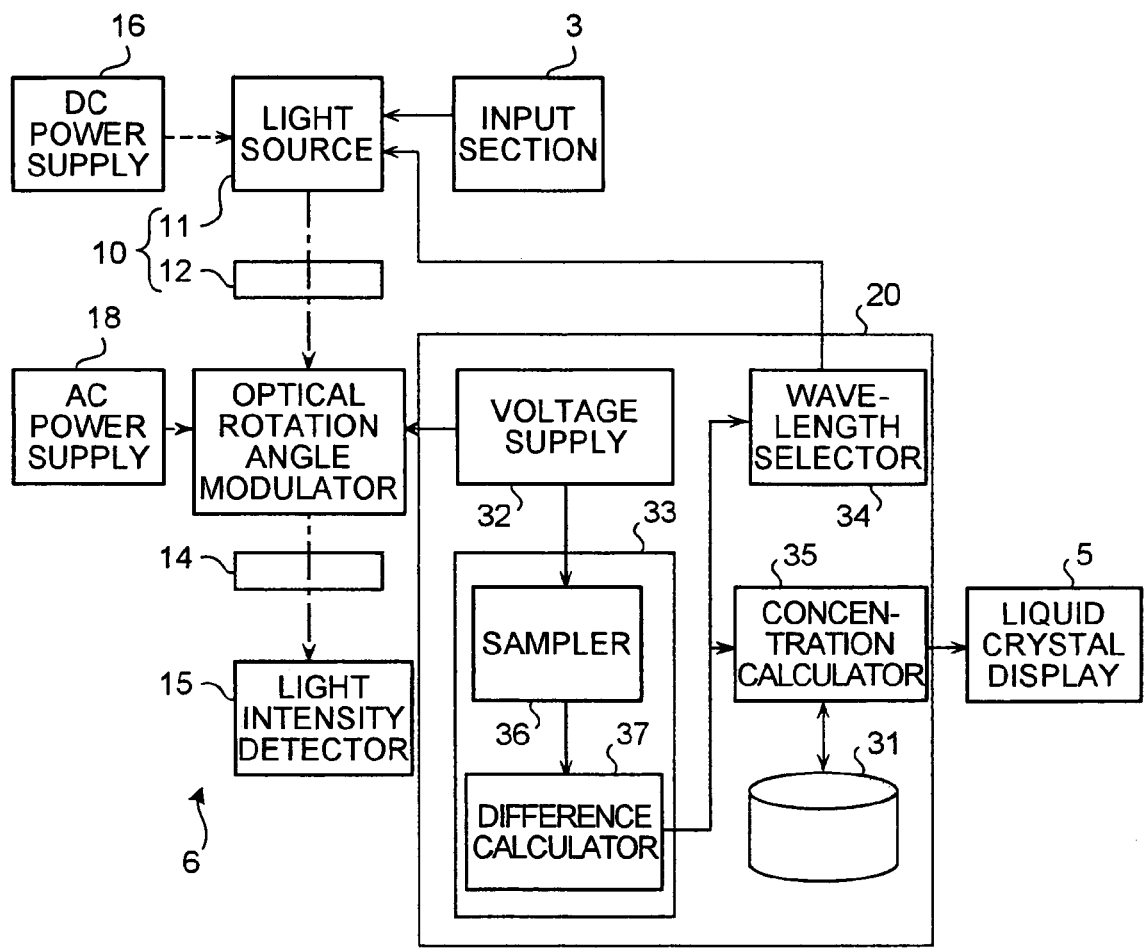
FIG. 4 is a block diagram of a functional configuration of the concentration measuring apparatus according to the first embodiment.

The control box 7 in FIG. 1 accommodates the dc power supply 16 for light source 11 and the ac power supply 18 for optical rotation angle modulator 13 in FIG. 2, and the controller 20, which is shown in FIGS. 3 and 4.

An explanation is given about the hardware configuration of the concentration measuring apparatus 1 according to the first embodiment, with reference to FIG. 3. The concentration measuring apparatus 1 includes the input section 3, liquid crystal display 5, linearly polarized light output section 10 (with light source 11 and first polarizer 12), optical rotation angle modulator 13, second polarizer 14, light intensity detector 15, dc power supply 16, and ac power supply 18, in addition to a controller 20. The controller 20 includes a CPU 21, a ROM 22, a RAM 23, and a bus 24 for their connection.

The CPU 21 governs an entirety of the controller 20. In the ROM 22 stores a concentration measuring program operable for measurement of concentration, as well as a later-described data table 31. The RAM 23 provides a work area for the CPU 21. FIG. 4 is a block diagram of a functional configuration of the controller 20.

Figure 5:
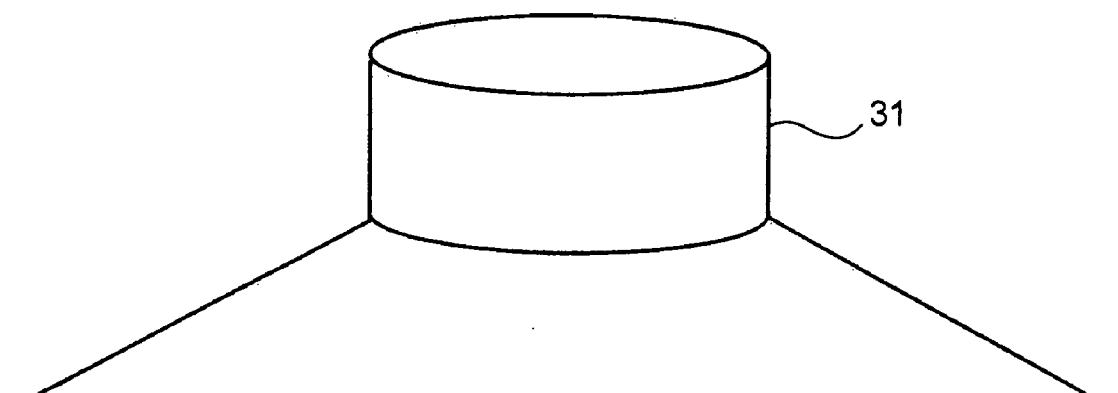
FIG. 5 explains contents of a data table of the concentration measuring apparatus according to the first embodiment.

As shown in FIG. 4, the controller 20 includes a data table 31, a voltage supply 32, a variation calculator 33, a wavelength selector 34, and a concentration calculator 35. The data table 31, as shown in FIG. 5, stores wavelengths of the laser beam La to be projected from the light source 11, and optical rotation coefficients proper to optically active substances contained in blood of physical body as the inspection object 100, to be set in a related manner.

In other words, the light source 11 may emit the laser beam La of any one of the wavelengths $\lambda 1$, $\lambda 2$, and $\lambda 3$.

The examples of the optically active substances contained in blood are glucose, plasma protein, and cholesterol. If glucose is used for the measurements, the optical rotation coefficients of the wavelengths $\lambda 1$, $\lambda 2$, and $\lambda 3$, are set to $\alpha 1$, $\alpha 2$, and $\alpha 3$ respectively. If plasma protein is used for the measurements, the optical rotation coefficients of the wavelengths $\lambda 1$, $\lambda 2$, and $\lambda 3$, are set to $\beta 1$, $\beta 2$, and $\beta 3$ respectively. If cholesterol is used for the measurements, the optical rotation coefficients of the wavelengths $\lambda 1$, $\lambda 2$, and $\lambda 3$, are set to $\gamma 1$, $\gamma 2$, and $\gamma 3$ respectively. The data table 31 is stored in either or both of the ROM 22 and the RAM 23.

When the command to start the measurement is output from the input section 3, and when the light intensity detector 15 detects insertion of the inspection object 100 in the inspection object insertion hole 4, the voltage supply 32 controls the ac power supply 18 so as to supply ac power to the optical rotation angle modulator 13. Moreover, the ac power supply 18 scans the ac voltage to be increased for a predetermined time interval, for example, one minute. The voltage supply 32 is adapted to exhibit its functions, for example, by the CPU 21 executing the concentration measuring program stored in the ROM 22, with support from the RAM 23, as shown in FIG. 3.

Figure 7:
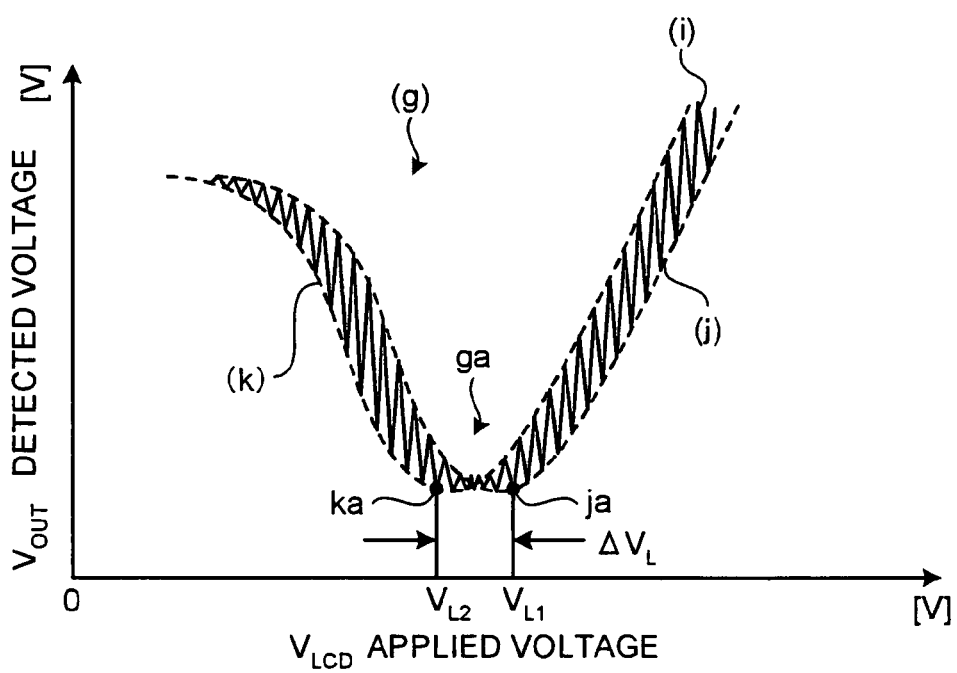
FIG. 7 is a detailed graph about extremum of the curve of FIG. 6.

The variation calculator 33 includes the sampler 36 and the difference calculator 37. The sampler 36 samples a voltage $V_{L1}$ applied in correspondence to a first optical rotation angle $\theta 1$, and a voltage $V_{L2}$ applied in correspondence to a second optical rotation angle $\theta 2$, see FIG. 7. As shown in FIG. 7, among intensities of light of waveforms (g) corresponding to optical rotation angles modulated by the optical rotation angle modulator 13, that of a waveform (j) is detected by the light intensity detector 15 at a maximum in amplitude of a pulsing waveform (i) of blood. The voltage $V_{L1}$ is sampled as an applied voltage when the detected intensity of light of the waveform (j) has an extremum ja.

Likewise, among intensities of light of waveforms (g) corresponding to optical rotation angles modulated by the optical rotation angle modulator 13, that of a waveform (k) is detected by the light intensity detector 15 at a minimum in amplitude of the pulsing waveform (i) of blood. The voltage $V_{L2}$ is sampled as an applied voltage when the detected intensity of light of the waveform (k) has an extremum ka.

The difference calculator 37 calculates a difference $\Delta V_L$ between the applied voltage $V_{L1}$ corresponding to the first optical rotation angle $\theta 1$, and the applied voltage $V_{L2}$ corresponding to the second optical rotation angle $\theta 2$, as they are sampled by the sampler 36. The difference $\Delta V_L$ corresponds to an amount of variation $\Delta \theta$ of optical rotation angle developed in light Ld transmitted through the inspection object 100, by pulsation of the pulsing component.

Information about a correlation between the difference $\Delta V_L$ and the optical rotation angle $\theta$ is stored in the ROM 22 or the RAM 23. Using this information, a specific difference $\Delta V_L$ can be converted into optical rotation angle $\theta$. The variation calculator 33 is adapted to exhibit its functions, for example, by the CPU 21 executing the concentration measuring program stored in the ROM 22 or the RAM 23 shown in FIG. 3.

The wavelength selector 34 controls waveform selection of the laser beam La to be projected from the light source 11. More specifically, the drive circuit of light source 11 has a plurality of modulating frequencies selective thereamong to change the wavelength of laser beam La to be projected from the laser diode, for example, from $\lambda 1$ to $\lambda 2$. The wavelength selector 34 is adapted to exhibit its functions, for example, by the CPU 21 executing the concentration measuring program stored in the ROM 22, with support from the RAM 23, as shown in FIG. 3.

The concentration calculator 35 calculates concentrations of optically active substances contained in a pulsing component of the inspection object 100, based on the variations $\Delta \theta$ calculated by the variation calculator 33 and the optical rotation coefficients of optically active substances stored in the date table 31. More specifically, the concentration calculator 35 reads a set of optical rotation coefficients $\alpha 1$, $\beta 1$, and $\gamma 1$ of respective optically active substances (glucose, plasma protein, and cholesterol) that correspond to a laser beam La projected with a wavelength $\lambda 1$ at the first time, that is, before a change of wavelength by the wavelength selector 34.

The read optical rotation coefficients $\alpha 1$, $\beta 1$, and $\gamma 1$, and a variation $\Delta \theta 1$ calculated at the variation calculator 33 along projection action of the laser beam La with wavelength $\lambda 1$ are substituted in an equation (2), $$\Delta \theta 1 = \alpha 1 \cdot C_{glu} \cdot \Delta L + \beta 1 \cdot C_{alb} \cdot \Delta L + \gamma 1 \cdot C_{cho} \cdot \Delta L \qquad (2),$$

where $C_{glu}$ is a concentration of glucose, $C_{alb}$ is a concentration of plasma protein, $C_{cho}$ is a concentration of cholesterol, and $\Delta L$ is a variation in length L of an optical path of light transmitted through the inspection object 100, that is, an amplitude of pulsing blood.

As a laser beam La is projected with a wavelength changed to $\lambda 2$ by the wavelength selector 34, there are read another set of optical rotation coefficients $\alpha 2$, $\beta 2$, and $\gamma 2$ of respective optically active substances (glucose, plasma protein, and cholesterol) that correspond to the laser beam La projected with the changed wavelength λ2.

The read optical rotation coefficients α2, β2, and γ2, and a variation Δθ2 calculated at the variation calculator 33 along projection of the laser beam La with wavelength λ2 are substituted in an equation (3), such that:

$$\Delta\theta2=\alpha2\cdot C_{glu}\cdot\Delta L+\beta2\cdot C_{alb}\cdot\Delta L+\gamma2\cdot C_{cho}\cdot\Delta L \quad (3),$$

As a laser beam La is projected with a wavelength yet changed to λ3 by the wavelength selector 34, there are read another set of optical rotation coefficients α3, β3, and γ3 of respective optically active substances (glucose, plasma protein, and cholesterol) that correspond to the laser beam La projected with the changed wavelength λ3.

The read optical rotation coefficients α3, β3, and γ3, and a variation Δθ3 calculated at the variation calculator 33 along projection of the laser beam La with wavelength λ3 are substituted in an equation (4), such that:

$$\Delta\theta3=\alpha3\cdot C_{glu}\cdot\Delta L+\beta3\cdot C_{alb}\cdot\Delta L+\gamma3\cdot C_{cho}\cdot\Delta L \quad (4),$$

The concentration calculator 35 solves a set of the simultaneous equations (2) to (4), thereby calculating concentrations of respective optically active substances.

The concentration calculator 35 is adapted to exhibit its functions, for example, by the CPU 21 executing the concentration measuring program stored in the ROM 22, with support from the RAM 23, as shown in FIG. 3.

Output characteristics of the light intensity detector 15 relative to voltages applied to the optical rotation angle modulator 13 will now be explained with reference to FIG. 6. As the voltage applied to the optical rotation angle modulator 13 is scanned, a varying intensity of light is output, for example, in a waveform (f) for an optically inactive inspection object. For an inspection object 100 with blood containing levorotatory optically active substances, the light intensity is output in a waveform (g) along a scan to the voltage applied to the optical rotation angle modulator 13. For an inspection object with blood containing optically active substances stronger in optical rotation than the inspection object 100 of waveform (g), the light intensity is output in a waveform (h) along a scan to the voltage applied to the optical rotation angle modulator 13.

The polarization axis of the second polarizer 14 is oriented so that the light intensity detector 15 has a minimum output $V_{OUT}$ in the waveform (f) when the voltage $V_{LCD}$ applied to the optical rotation angle modulator 13 is set to a 0 V (an initial state). For the waveform (g), the output $V_{OUT}$ is kept from becoming a minimum in the initial state by the optically active inspection object 100, but has a minimal extremum ga when the light Ld transmitted through the inspection object 100 has an optical axis coincident in orientation with the axis of absorption of the second polarizer 14, as the applied voltage $V_{LCD}$ is varied.

For the waveform (h), which is of light intensities output along a scan to the voltage $V_{LCD}$ applied to the optical rotation angle modulator 13 for an inspection object with blood containing optically active substances yet stronger in optical rotation than the inspection object 100 of waveform (g), the output $V_{OUT}$ has an extremum ha yet shifted toward a high voltage end.

Figure 6:
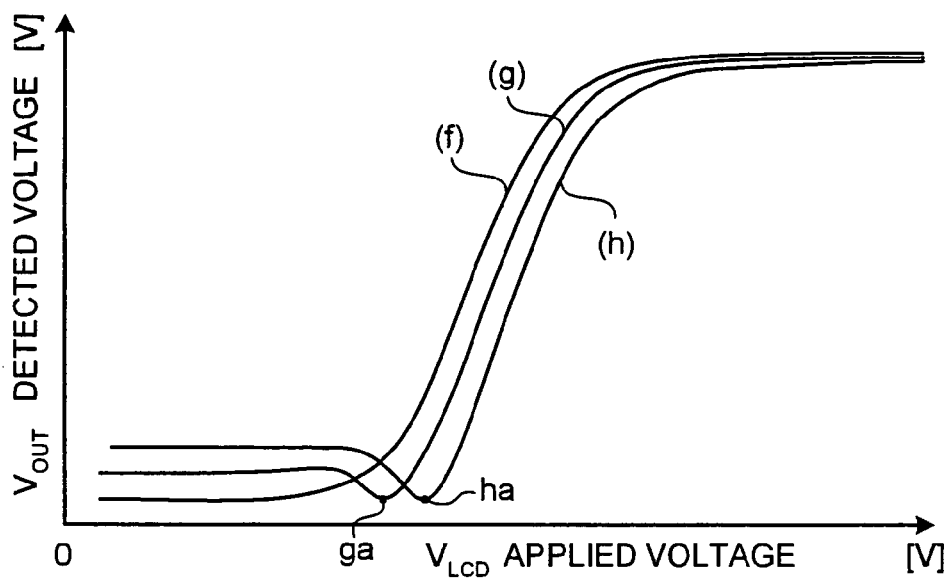
FIG. 6 is a graph of a detected voltage vs. applied voltage characteristic curve of the concentration measuring apparatus according to the first embodiment.

FIG. 7 is an enlarged portion near the extremum ga of waveform (g) in FIG. 6. Optically active substances such as glucose reside in tissue cells and blood. Those in cells of tissue (e.g. skin) have their influences, which are eliminated in order for concentrations of optically active substances such as glucose, plasma protein, and cholesterol contained simply in blood to be measured, by making use of a pulsing component.

The light Ld is transmitted through a physical body 100, along an optical path, of which the length L is varied by ΔL in blood, in response to a pulsation of the blood, with a resultant variation Δθ in optical rotation angle θ, which is followed by a variation of extremum in the output $V_{OUT}$. As the scan to $V_{LCD}$ in FIG. 6 is performed with a sufficiently lower speed than the pulsation, as shown in FIG. 7, the waveform (g) has an amplitude widen to some extent about the extremum ga. This is because of a variation in detected voltage $V_{OUT}$ due to the variation Δθ of optical rotation angle θ caused by increase and decrease of the pulsing component.

Accordingly, the waveform (g) is shaped with a certain width, to be given as a waveform (j) when a pulsing waveform (i) has a maximum amplitude, and as a waveform (k) when the pulsing waveform (i) has a minimum amplitude, whereby the variation Δθ due to optically active substances in the pulsing component is related to a variation $\Delta V_L$ to be the difference between an extremum ja in the waveform (j), where the transition of extremum ga becomes maximum, and an extremum ka in the waveform (k), where the transition of extremum ga becomes minimum. The use of variation Δθ allows for the measurement to be simply made of blood, without disturbances such as from tissue cells.

Figure 8:
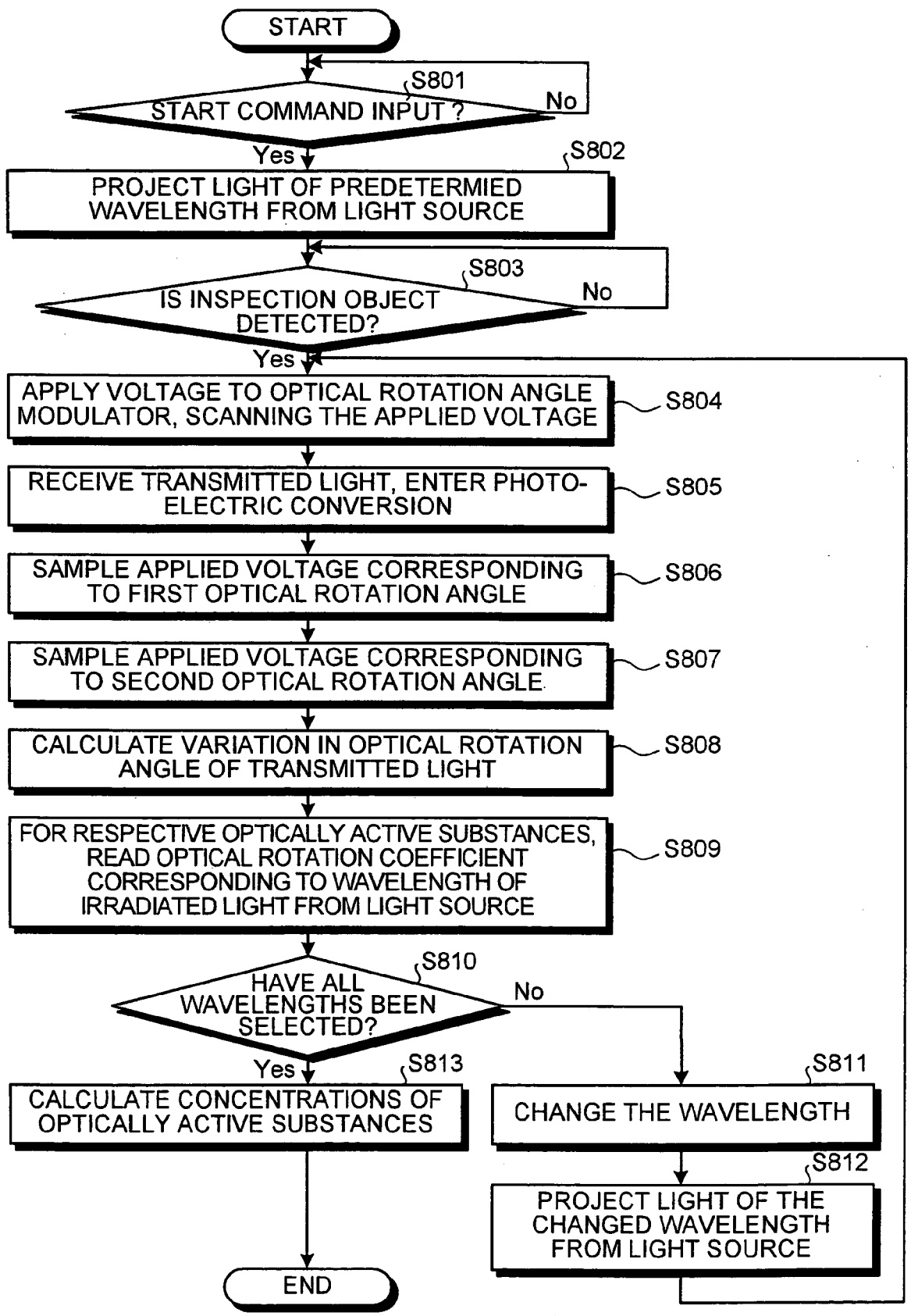
FIG. 8 is a flowchart that shows a control of the concentration measuring apparatus according to the first embodiment.

The functioning of the apparatus of the first embodiment will now be explained with reference to a flowchart of FIG. 8. The wavelength of laser beam La to be projected from the light source 11 is set to λ1, and changeable by selection in the order of λ1, λ2, and λ3. First, with the measurement start indicated by the input section 3 (step S801: Yes), the light source 11 projects a laser beam La of wavelength λ1 (step S802). Then, a decision is made of whether an inspection object 100 is inserted in the inspection object insertion hole 4 (step S803). This decision is based on a variation in level of the intensity of light detected by the light intensity detector 15.

Upon detection of an inserted inspection object 100 (step S803: Yes), a voltage is applied to the optical rotation angle modulator 13, while the applied voltage is scanned for a predetermined time (step S804), whereby the laser beam La projected from the light source 11 is output as a linearly polarized light Lb by the first polarizer 12, and the linearly polarized light Lb is incident on the optical rotation angle modulator 13, where, as the applied voltage is scanned, the incident light follows the applied voltage to have its optical axis rotated. As a result, light Lc, linearly polarized or elliptically polarized in dependence on the applied voltage, is emitted from the optical rotation angle modulator 13 to the inserted inspection object (the tip of finger) 100.

For the presence of optically active substances in blood and tissue cells in the human body, transmitted light Ld transmitted through the inspection object 100 has its optical axis direction or major axis direction rotated relative to an optical axis direction or major axis direction that the polarized light Lc has when emitted from the optical rotation angle modulator 13, for example, by presence of glucose, it is optically rotated to the left when facing the advancing direction of light, that is, dextro-rotated.

The light Ld transmitted through the inspection object 100 is received by the light intensity detector 15, where it is photoelectrically converted into a detected voltage $V_{OUT}$ (step S805). Thereafter, among optical rotation angles modulated by the optical rotation angle modulator 13, there is sampled a first optical rotation angle θ1 for an extremum to be matured of the intensity of light detected by the light intensity detector 15 when the pulsing component has a maximum amplitude (step S806). The first optical rotation angle θ1 corresponds to an applied voltage $V_{L1}$ at an extremum ja of an output waveform (j) in the waveform (j) shown in FIG. 7.

Likewise, among the optical rotation angles modulated by the optical rotation angle modulator 13, there is sampled a second optical rotation angle θ2 for an extremum to be matured of the intensity of light detected by the light intensity detector 15 when the pulsing component has a minimum amplitude (step S807). The second optical rotation angle θ2 corresponds to an applied voltage $V_{L2}$ at an extremum ka of an output waveform (k) in the waveform (k) shown in FIG. 7.

There is then calculated a difference $\Delta V_L$ between the first optical rotation angle θ1 (applied voltage $V_{L1}$) sampled at the step S806 and the second optical rotation angle θ2 (applied voltage $V_{L2}$) sampled at the step S807 (step S808). The difference $\Delta V_L$ is given as a variation Δθ1 of optical rotation angle in the transmitted light Ld transmitted through the inspection object 100.

The data table 31 is used to read therefrom, for respective optically active substances, optical rotation coefficients α1, β1, and γ1 corresponding to the wavelength λ1 of laser beam projected from the light source 11 (step S809). Then, a decision is made of whether the wavelength of laser beam is changed by selection (step S810). Unless the wavelength selection is finished (step S810: No), the wavelength of laser beam is changed from λ1 to λ2 (step S811). Then, with the changed wavelength λ2, a laser beam is projected from the light source 11 (step S812).

For the laser beam of wavelength λ2 also, respective processes at the steps S804 to S809 are repeated to thereby calculate a variation Δθ2, and read, from the data table 31, optical rotation coefficients α2, β2, and γ2 corresponding to the wavelength λ2 of laser beam. Then, another decision is made of whether the wavelength of laser beam is changed by selection (step S810).

Unless the wavelength selection is finished (step S810: No), the wavelength of laser beam is changed from λ2 to λ3 (step S811). Then, with the changed wavelength λ3, a laser beam is projected from the light source 11 (step S812). For the laser beam of wavelength λ3 also, respective processes at the steps S804 to S809 are repeated to thereby calculate a variation Δθ3, and read, from the data table 31, optical rotation coefficients α3, β3, and γ3 corresponding to the wavelength λ3 of laser beam.

At the step S810, as the wavelength selection is finished, that is, the selection has been made up to the wavelength λ3 (step S810: Yes), the calculated variation Δθ1 and read optical rotation coefficients α1, β1, and γ1 are substituted in the equation (2). Likewise, the calculated variation Δθ2 and read optical rotation coefficients α2, β2, and γ2 are substituted in the equation (3). Further, the calculated variation Δθ3 and read optical rotation coefficients α3, β3, and γ3 are substituted in the equation (4). There are thereby calculated respective concentrations of glucose, plasma protein, and cholesterol (step S813).

According to the first embodiment, detected voltages $V_{OUT}$ detected by the light intensity detector 15 detecting the intensity of light transmitted through an inspection object 100 are plotted as a graph to applied voltages $V_{LCD}$ applied to the optical rotation angle modulator 13, and a variation Δθ in optical rotation angle by optically active substances in a pulsing component of the inspection object 100 is read from extrema of graphed waveforms, to thereby measure concentrations of the optically active substances in the pulsing component.

It is thereby allowed to measure concentrations simply of optically active substances contained in the pulsing component, free from influences of optically active substances in other components than the pulsing component of the inspection object 100. As the optical rotation angle is used, there are no influences of absorption by other substances.

For the use of a TN liquid crystal cell as the optical rotation angle modulator 13, its optical rotatory nature or birefringence allows for the concentration measuring apparatus 1 to be made very compact and lightweight, with reduced power consumption.

Description is now made of a case of a scan to be performed to the applied voltage $V_{LCD}$ to the optical rotation angle modulator 13, with a sufficiently faster speed than the pulsation. The inspection object 100 is assumed to pulse approximately 60 times per one minute, so that a pulse 38 in FIG. 9 has a pulsing period T of approximately one second.

Accordingly, within the pulsing period T, the applied voltage $V_{LCD}$ is scanned 10 times or more in an applied voltage region including extremum ga of the waveform (g) (or waveform (h)) in FIG. 6. A scan of applied voltage $V_{LCD}$ at a pulse point p in FIG. 9 gives a waveform P in FIG. 10, which is a waveform when blood vessels are contracted to the end.

Figure 9:
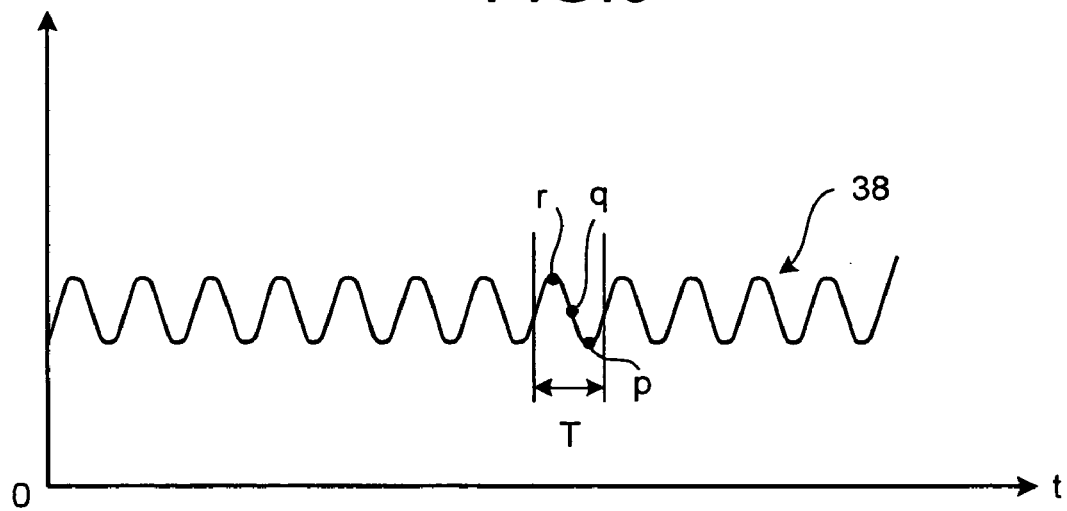
FIG. 9 is a graph of a pulsing waveform of an inspection object.
Figure 10:
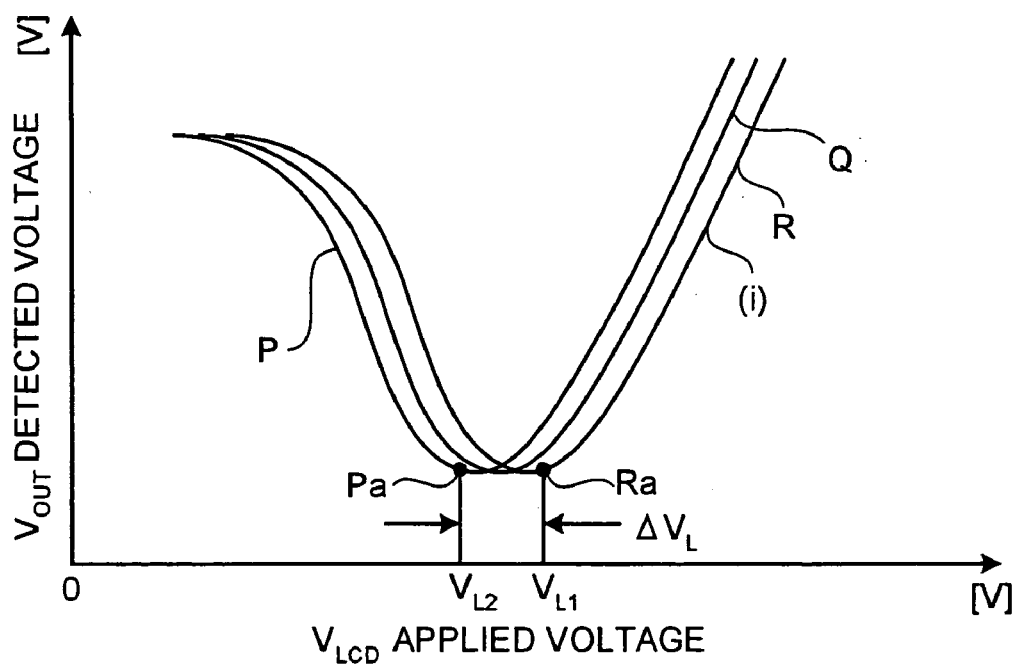
FIG. 10 is a graph of a detected voltage vs. applied voltage characteristic curve of the concentration measuring apparatus according to the first embodiment.

A scan of applied voltage $V_{LCD}$ at a pulse point q in FIG. 9 gives a waveform Q in FIG. 10. A scan of applied voltage $V_{LCD}$ at a pulse point r in FIG. 9 gives a waveform R in FIG. 10, which is a waveform when the blood vessels are expanded to the end. The waveform P has an extremum Pa at an applied voltage $V_{L2}$, and the waveform R has an extremum Ra at an applied voltage $V_{L1}$. The variation Δθ is calculated in terms of a voltage $\Delta V_L$ as the difference between applied voltages $V_{L1}$ and $V_{L2}$.

Figure 11:
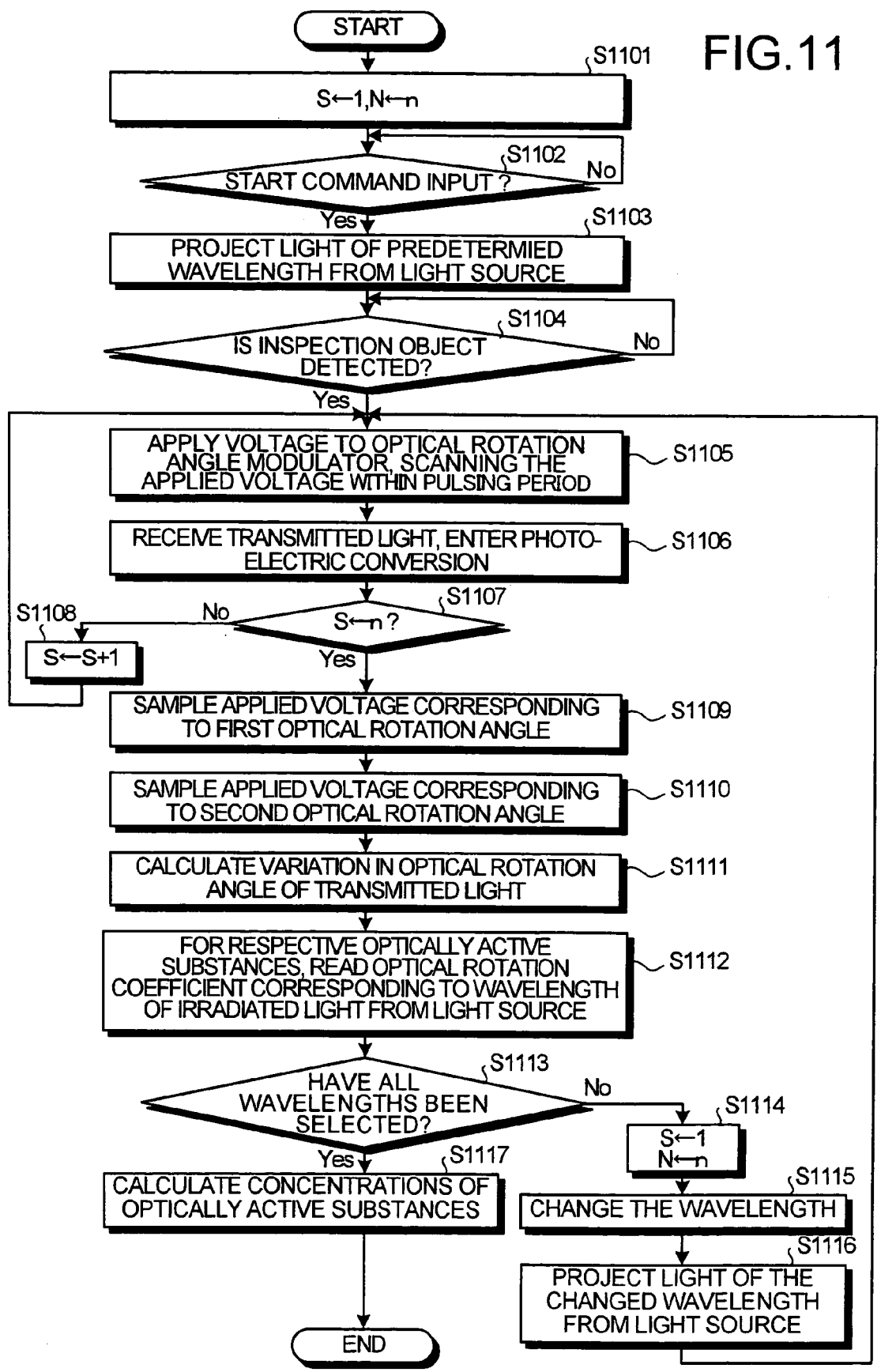
FIG. 11 is a flowchart of another control of the concentration measuring apparatus according to the first embodiment.

Referring now to a flowchart of FIG. 11, explanation is given about actions and processes in the case of a scan to be performed to the applied voltage $V_{LCD}$ to the optical rotation angle modulator 13, with a sufficiently faster speed than the pulsation. The wavelength of laser beam La to be projected from the light source 11 is set to λ1, and changeable by selection in the order of λ1, λ2, and λ3. First, the optical rotation angle modulator 13 has a number S of times of scan and a limit N to the scan time number set thereto such that S=1 and N=n (step S1101). With the measurement start input at the input section 3 (step S1102: Yes), the light source 11 projects a laser beam La of wavelength λ1 (step S1103).

Thereafter, a decision is made of whether an inspection object 100 is inserted in the inspection object insertion hole 4 (step S1104). This decision is based on a variation in level of the intensity of light detected by the light intensity detector 15. Upon detection of an inserted inspection object 100 (step S1104: Yes), a voltage is applied to the optical rotation angle modulator 13, while the applied voltage $V_{LCD}$ is scanned once within the pulsing period T (step S1105).

The laser beam La projected from the light source 11 is output as a linearly polarized light Lb by the first polarizer 12, and the linearly polarized light Lb is incident on the optical rotation angle modulator 13, where, as the applied voltage is scanned, the incident light follows the applied voltage $V_{LCD}$ to have its optical axis rotated. As a result, light Lc, linearly polarized or elliptically polarized in dependence on the applied voltage $V_{LCD}$, is emitted from the optical rotation angle modulator 13 to the inserted inspection object (the tip of finger) 100.

For the presence of optically active substances in blood and tissue cells in the human body, transmitted light Ld transmitted through the inspection object has its optical axis direction or major axis direction rotated relative to an optical axis direction or major axis direction that the polarized light Lc has when emitted from the optical rotation angle modulator 13, for example, by presence of glucose, it is optically rotated to the left when facing the advancing direction of light, that is, dextro-rotated.

The light Ld transmitted through the inspection object 100 is received by the light intensity detector 15, where it is photo-electrically converted into a detected voltage $V_{OUT}$ (step S1106). Then, a decision is made of whether the scan time number S has reached the limit n (step S1107). Unless the limit is reached (step S1107: No), the scan time number S is incremented (step S1108) to execute the steps S1105 and S1106.

If the scan time number S has reached the limit n (step S1107: Yes), there is sampled, among optical rotation angles (as scanned voltages) modulated by the optical rotation angle modulator 13, a first optical rotation angle θ1 for an extremum Ra to be matured in the output waveform R (see FIG. 10) when the pulse 38 has a maximum amplitude r (see FIG. 9), that is, the applied voltage $V_{L1}$ (step S1109).

Likewise, among the optical rotation angles (as scanned voltages) modulated by the optical rotation angle modulator 13, there is sampled a second optical rotation angle θ2 for an extremum Pa to be matured in the output waveform P (see FIG. 10) when the pulse 38 has a minimum amplitude p (see FIG. 9), that is, the applied voltage $V_{L2}$ (step S1110).

There is then calculated a difference $\Delta V_L$ between the first optical rotation angle θ1 (applied voltage $V_{L1}$) sampled at the step S1109 and the second optical rotation angle θ2 (applied voltage $V_{L2}$) sampled at the step S1110. The difference $\Delta V_L$ is given as a variation Δθ1 of optical rotation angle in the transmitted light Ld transmitted through the inspection object 100.

The data table 31 is used to read therefrom, for respective optically active substances, optical rotation coefficients α1, β1, and γ1 corresponding to the wavelength λ1 of laser beam projected from the light source 11 (step S1112). Then, a decision is made of whether the wavelength selection is finished (step S1113). Unless the wavelength selection is finished (step S1113: No), the scan time number S and the limit N are reset, so that S=1 and N=n (step S1114).

The wavelength of laser beam is changed from λ1 to λ2 (step S1115). With the changed wavelength λ2, a laser beam is projected from the light source 11 (step S1116). For the laser beam of wavelength λ2 also, respective processes at the steps S1105 to S1112 are repeated to thereby calculate a variation Δθ2, and read, from the data table 31, optical rotation coefficients α2, β2, and γ2 corresponding to the wavelength λ2 of laser beam.

It is decided whether all the wavelengths have been selected (step S1113). If all the wavelength have not be selected (step S1113: No), the scan time number S and the limit N are reset, so that S=1 and N=n (step S1114). Then, the wavelength of laser beam is changed from λ2 to λ3 (step S1115).

With the changed wavelength λ3, a laser beam is projected from the light source 11 (step S1116). For the laser beam of wavelength λ3 also, respective processes at the steps S1105 to S1112 are repeated to thereby calculate a variation Δθ3, and read, from the data table 31, optical rotation coefficients α3, β3, and γ3 corresponding to the wavelength λ3 of laser beam.

At the step S1113, as there is no wavelength that has not been selected, that is, the selection has been made up to the wavelength λ3 (step S1113: Yes), the calculated variation Δθ1 and read optical rotation coefficients α1, β1, and γ1 are substituted in the equation (2). Likewise, the calculated variation Δθ2 and read optical rotation coefficients α2, β2, and γ2 are substituted in the equation (3). Further, the calculated variation Δθ3 and read optical rotation coefficients α3, β3, and γ3 are substituted in the equation (4). There are thereby calculated respective concentrations of glucose, plasma protein, and cholesterol (step S1117).

As described, detected voltages $V_{OUT}$ detected by the light intensity detector 15 detecting the intensity of light transmitted through an inspection object 100 are plotted as a graph to applied voltages $V_{LCD}$ applied to the optical rotation angle modulator 13, and a variation Δθ in optical rotation angle by optically active substances in a pulsing component of the inspection object 100 is read from extrema of graphed waveforms, to thereby measure concentrations of the optically active substances in the pulsing component.

Thus, it is possible to measure concentrations of only optically active substances contained in the pulsing component of the inspection object 100. This measurement is not influenced by the optically active substances that are present in other components than the pulsing component. As the optical rotation angle is used, this measurement is not influenced by absorption by other substances.

A TN liquid crystal cell may be used as the optical rotation angle modulator 13. By the uses of optical rotatory nature or birefringence of the TN liquid crystal cell, the concentration measuring apparatus 1 can be made very compact and lightweight, with reduced power consumption. Further, in the case of a scan to be performed to the applied voltage $V_{LCD}$ to the optical rotation angle modulator 13, with a sufficiently faster speed than the pulsation, the measurement can be performed within the pulsing period, allowing measurements to be performed in shorter time.

Figure 12:
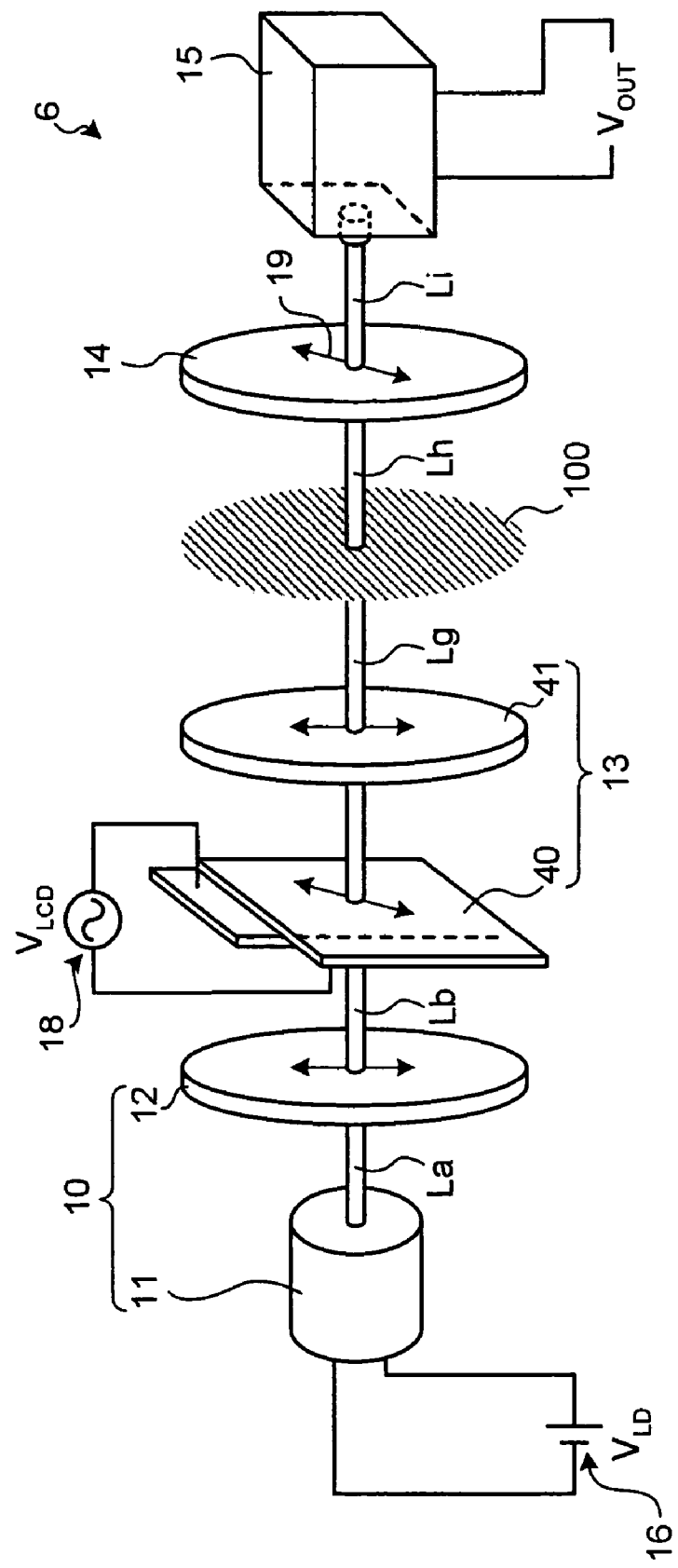
FIG. 12 is a schematic perspective view of a measuring system of a concentration measuring apparatus according to a second embodiment of the present invention.

A concentration measuring apparatus and a concentration measuring method according to a second embodiment of the present invention will now be explained using FIG. 12. In the second embodiment, the optical rotation angle modulator 13 is configured with a homogeneous liquid crystal cell 40 and a λ/4 wavelength polarizer 41. The rest of configuration is identical to the first embodiment, and redundant description is omitted.

Linearly polarized light Lb output from the linearly polarized light output section 10 is incident on the homogeneous liquid crystal cell 40. The homogenous liquid crystal cell 40 and the λ/4 wavelength polarizer 41 are configured for modulation of the incident linearly polarized light Lb to provide linearly polarized light Lg with a modulated optical rotation angle. The λ/4 wavelength polarizer 41 emits the linearly polarized light Lg with modulated optical rotation angle to the inspection object 100.

If the light incident on the inspection object 100 is elliptically polarized, sometimes that light receives an additional influence of elliptic polarization superposed thereon due to transmission through the inspection object 100. As a result, there is a great chance of reduction in detection sensitivity of the light intensity detector 15. However, at least incident light Lg on the inspection object 100 is linearly polarized, so that light Lh transmitted through the inspection object 100 is elliptically polarized from linearly polarized light or incident linearly polarized light Lb, to be detected as elliptically polarized light Li. Therefore, the light intensity detector 15 has improved detection sensitivity, allowing for concentrations of optically active substances to be calculated with an improved precision.

The use of homogeneous liquid crystal cell 40 and λ/4 wavelength polarizer 41 in the optical rotation angle modulator 13, as well as its birefringence, allows for the concentration measuring apparatus 1 to be made very compact and lightweight, with reduced power consumption.

Figure 13:
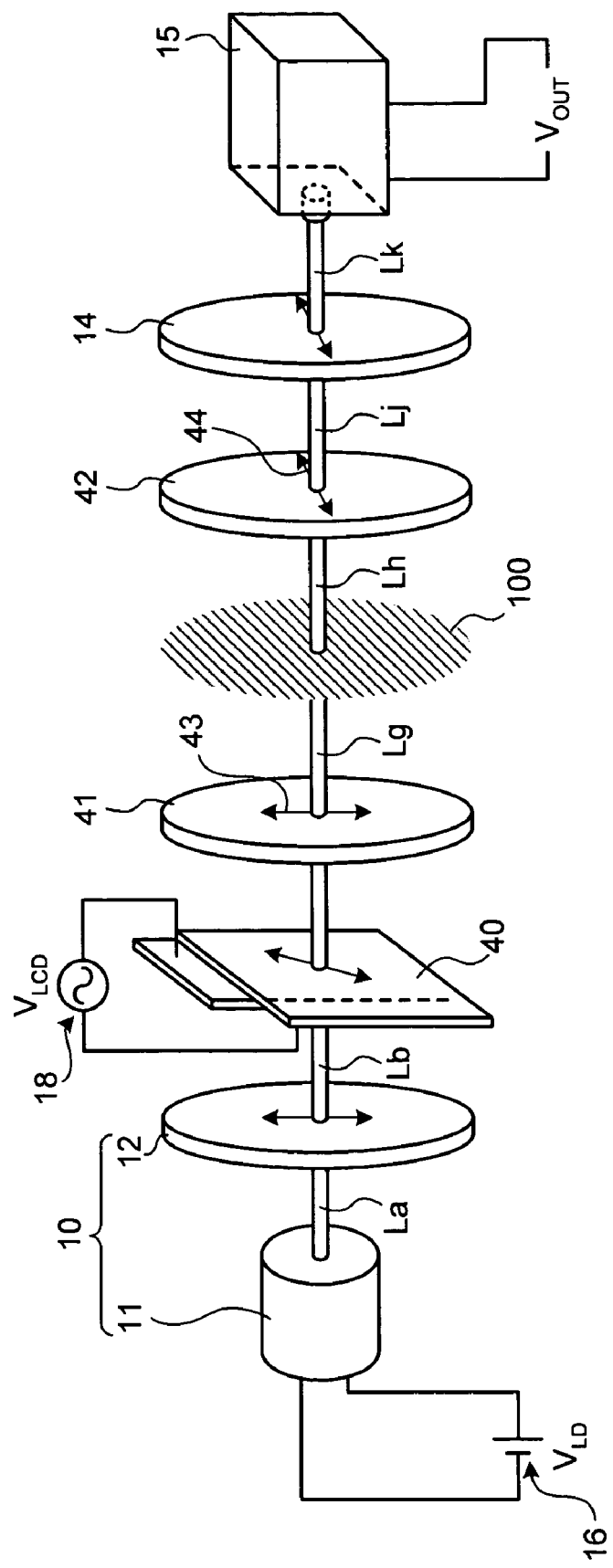
FIG. 13 is a schematic perspective view of a measuring system of a concentration measuring apparatus according to a third embodiment of the present invention.

A concentration measuring apparatus and a concentration measuring method according to a third embodiment of the present invention will now be explained using FIG. 13. In the third embodiment, the optical rotation angle modulator 13 is configured with a homogeneous liquid crystal cell 40, and a pair of first and second λ/4 wavelength polarizers 41 and 42 arranged with the inspection object insertion hole 4 in between. The rest of configuration is identical to the first embodiment, and redundant description is omitted.

On the homogeneous liquid crystal cell 40 is incident linearly polarized light Lb output from the linearly polarized light output section 10. The homogenous liquid crystal cell 40 and the first λ/4 wavelength polarizer 41 are configured for modulation of the incident linearly polarized light Lb to provide linearly polarized light Lg with a modulated optical rotation angle. The first λ/4 wavelength polarizer 41 emits the linearly polarized light Lg with modulated optical rotation angle to the inspection object 100.

The first λ/4 wavelength polarizer 41 has a first optical axis 43 oriented in a predetermined direction. The second λ/4 wavelength polarizer 42 has a second optical axis 44 perpendicular to the first optical axis 43. Transmitted light Lh from the inspection object 100 is incident on the second λ/4 wavelength polarizer 42, and emitted therefrom as linearly polarized light Lj to the second polarizer 14. Light Lk transmitted through the second polarizer 14 is emitted to the light intensity detector 15.

According to the third embodiment, the second optical axis 44 of the second λ/4 wavelength polarizer 42 is oriented perpendicular to the first optical axis 43 of the first λ/4 wavelength polarizer 41. As a result, the second λ/4 wavelength polarizer 42 cancels the retardation resulting due to the first λ/4 wavelength polarizer 41 and thereby it becomes possible to suppress the changes in the characteristics due to change in temperature in the surrounding area. Thus, the sensitivity of the light intensity detector 15 can be improved and it becomes possible to calculate concentrations of optically active substances with greater precision.

The use of homogeneous liquid crystal cell 40 in the optical rotation angle modulator 13, as well as its birefringence, allows for the concentration measuring apparatus 1 to be made very compact and lightweight, with reduced power consumption.

A concentration measuring apparatus and a concentration measuring method according to a fourth embodiment of the present invention will now be described using FIG. 14. In the fourth embodiment, the measuring system 6 is configured with a lens system. The rest of configuration is identical to the first embodiment, and redundant description is omitted.

Figure 14:
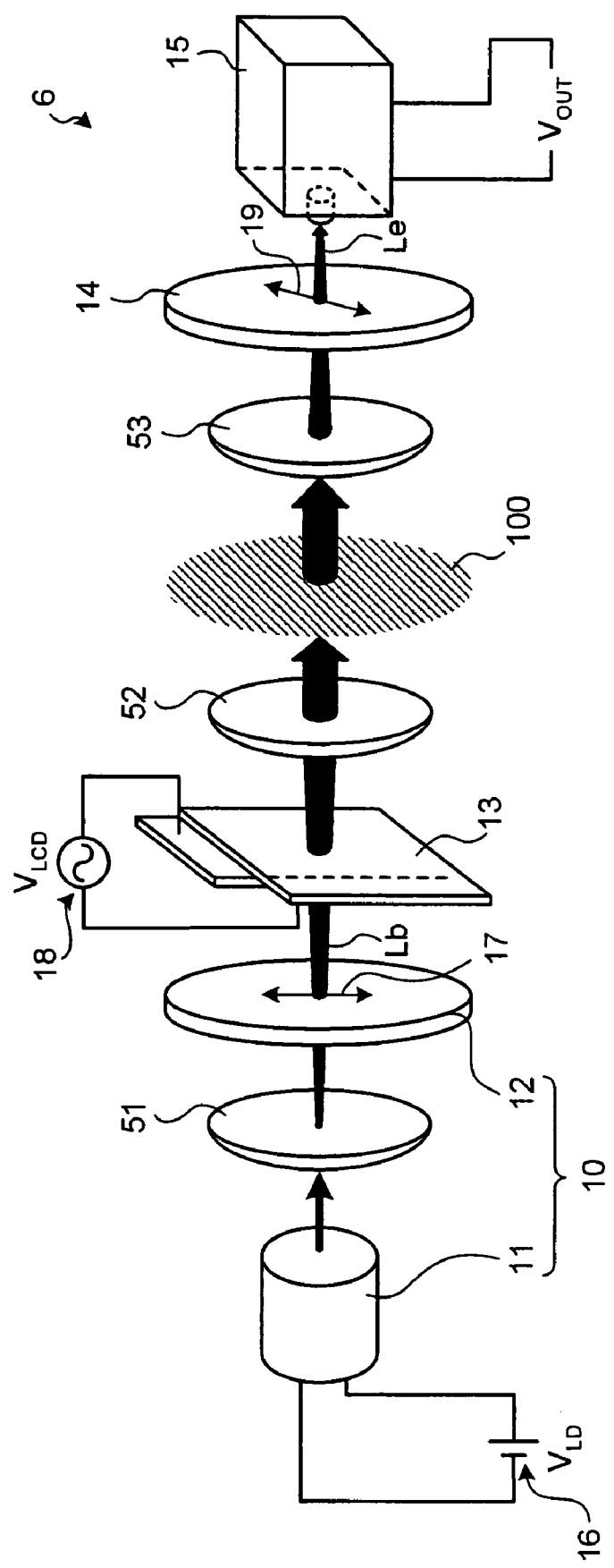
FIG. 14 is a schematic perspective view of an example of a measuring system of a concentration measuring apparatus according to a fourth embodiment of the present invention.

As shown in FIG. 14, the lens system is provided in the measuring system 6 of the concentration measuring apparatus 1 shown in FIG. 2 according to the first embodiment.

As shown in FIG. 14, the lens system includes three lenses: a first lens 51, a second lens 52, and a third lens 53. The first lens 51 is interposed between the light source 11 and the first polarizer 12, for adjustment of light beam projected from the light source 11 to have a predetermined beam diameter, so that projected light on the optical rotation angle modulator 13 can be adjusted adequate in quantity of light. If the light beam projected from the light source 11 is relatively small in diameter, the first lens 51 may be configured with an adequate tendency to expand the beam diameter.

The second lens 52 receives light emitted from the optical rotation angle modulator 13, to emit as collimated light to the inspection object 100. The second lens 52 thus controls the divergence of light diverged by the first lens 51, for emission to the inspection object 100, and is provided as necessary.

The third lens 53 is configured for collection of the transmitted light Ld from the inspection object 100 to the light intensity detector 15. The third lens 53 can do in any position if its focal point coincides on the light intensity detector 15, and may be located before the second polarizer 14 or between the second polarizer 14 and the light intensity detector 15.

According to the fourth embodiment, more light can be incident on the optical rotation angle modulator 13, to be averaged over whole liquid crystal molecules within a projected region of incident light, with reduced influences from fluctuating individual liquid crystal molecules, allowing for stable emission of light to the inspection body 100. Much light can be incident on the optical rotation angle modulator 13 from small light source 11, with reduced power consumption.

If the light beam projected from the light source 11 is relatively large in diameter, the first lens 51 may be configured with an adequate tendency to contract the beam diameter. The first lens 51 may be eliminated, if the beam diameter of projected light La is adaptive at the light intensity detector 15 for adequate detection with good precision.

The third lens 53 may be disposed in front of the inspection object 100 with respect to the light source 11, and set in position adjusted in consideration such as of a focal distance of the second lens 52, to prevent reduction in the intensity of projected light on the inspection object 100, thereby allowing for measurement even if the light absorption of inspection object 100 is relatively high.

Figure 15:
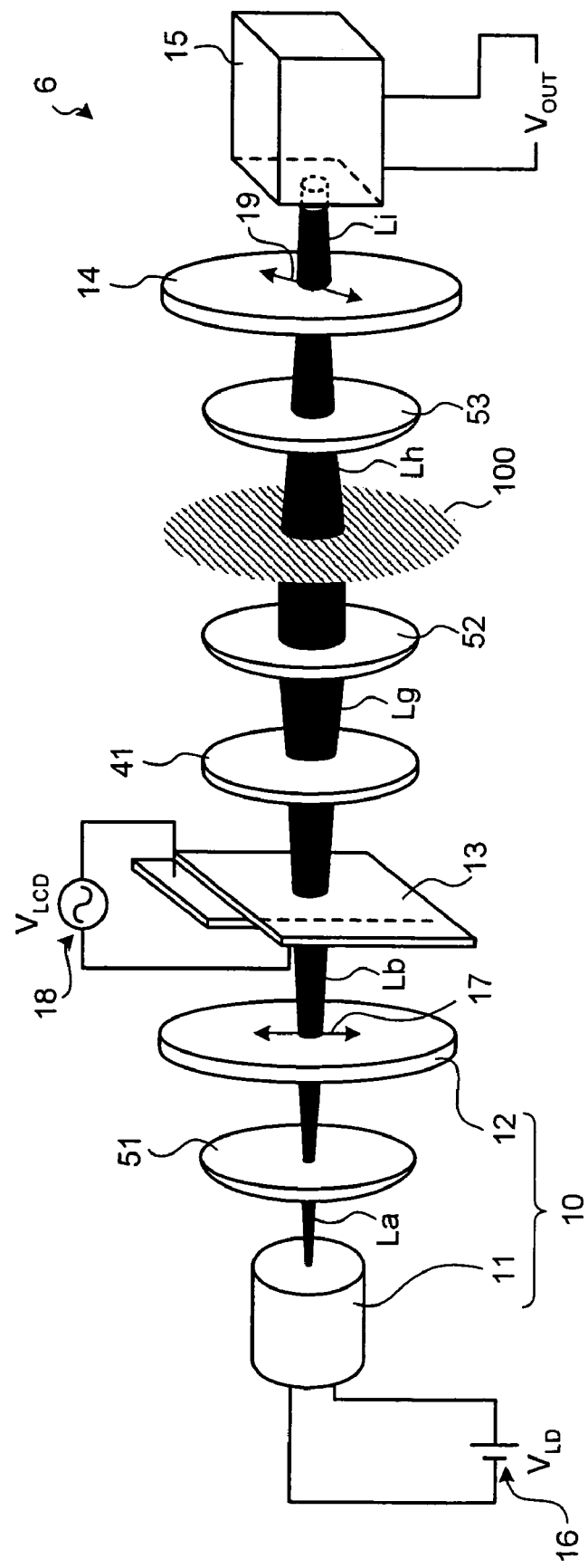
FIG. 15 is a schematic perspective view of another example of a measuring system of a concentration measuring apparatus according to the fourth embodiment.
Figure 16:
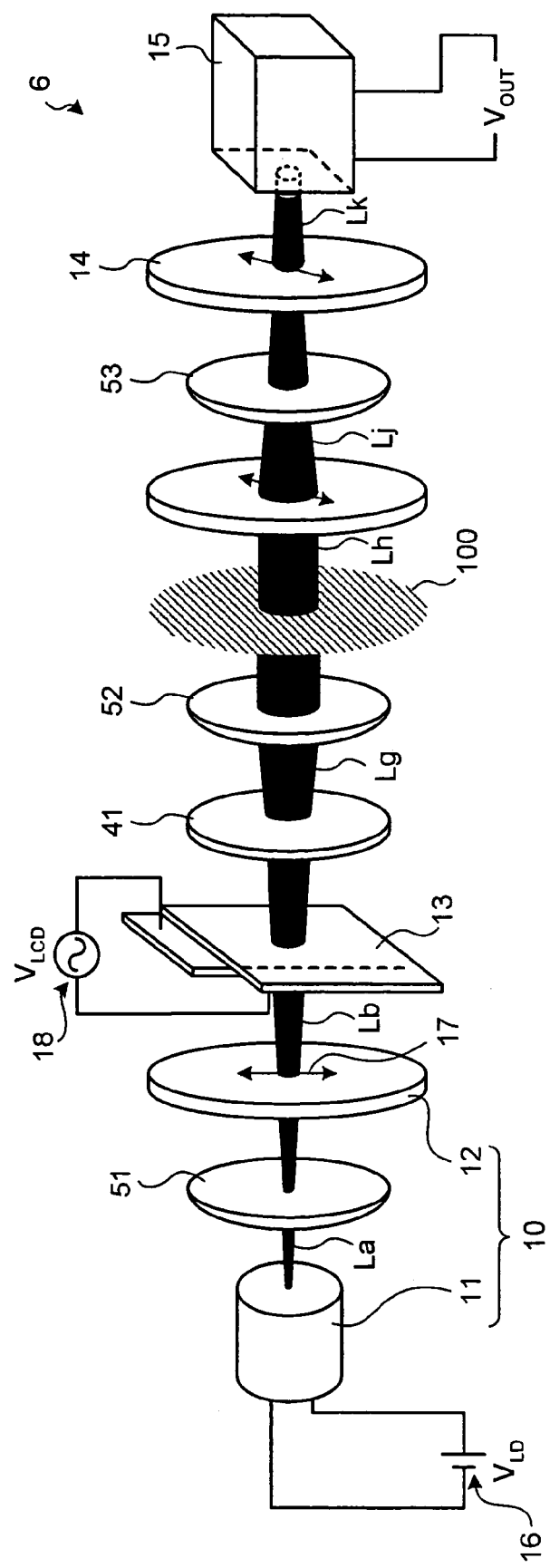
FIG. 16 is a schematic perspective view of still another example of a measuring system of a concentration measuring apparatus according to the fourth embodiment.

In the fourth embodiment, the lens system is provided in the measuring system 6 of the concentration measuring apparatus 1 according to the first embodiment. In this respect, as shown in FIG. 15 and 16 respectively, the concentration measuring apparatuses 1 according to the second or third embodiment may also have a lens system provided in the measuring system 6. In that case, the third lens 53 may preferably be disposed between the inspection object 100 end the second polarizer 14 as in FIG. 15, between the inspection object 100 and the second λ/4 wavelength polarizer 42, between the second λ/4 wavelength polarizer 42 and the second polarizer 14 as in FIG. 16, or between the second polarizer 14 and the light intensity detector 15.

In the fourth embodiment, the lens system is described simply for illustrative purpose. The lens system including lens 51 to 53 may preferably be modified, for example, in type and number of lens, as necessary for divergence and convergence of light beam projected from the light source 11, as well as in arrangement of lens to be adaptive for the condition of measurement. It is thus noted that, in the embodiment or modification described, the type and number of lens 51 to 53, as well as the arrangement of lens, are illustrative, not restrictive, and may be modified or changed.

It has been mentioned above to use a TN liquid crystal cell or a homogeneous liquid crystal cell 40 and a λ/4 wavelength polarizer as the optical rotation angle modulator 13. However, the optical rotation angle modulator 13 may be configured with a Faraday cell or a Pockels cell.

In practical medical services, individual patients have their biological data, and the measurement of blood sugar level needs an attacking method, as well. Measured blood sugar levels by practical attacking methods may preferably be corrected by measurements using the concentration measuring apparatus 1 according to any of the embodiments described, to obtain good precision of blood sugar level, allowing for blood collection, as compared with dedicated cases to attacking methods, to be reduced in number of times, such as once per every month or after a relatively long interval, or limited to an initial measurement, with reduced burden on the physical body.

As will be apparent from the foregoing description, a concentration measuring apparatus and a concentration measuring method according to the invention is adapted to measure a concentration of an optically active substance in a pulsing component of an inspection object, with high precision.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. A concentration measuring apparatus comprising:
a linearly polarized light supplier that supplies linearly polarized light;
an optical rotation angle modulator that modulates an optical rotation angle of the linearly polarized light to obtain modulated light;
a light intensity detector that detects an intensity of light coming out of an inspection object when the modulated light is passed through the inspection object, wherein an optically active substance in the inspection object optically rotates the modulated light when the modulated light passes through the inspection object;
a variation calculator that calculates a variation in the optical rotation angle of the light coming out of the inspection object based on an angle to which the optical rotation angle modulator has modulated the linearly polarized light and the intensity of the light detected by the light intensity detector, wherein the optical rotation angle of the light coming out of the inspection object varies in response to a pulsation of a pulsing component of the inspection object; and
a concentration calculator that calculates a concentration of the optically active substance based on the variation in the optical rotation angle,
wherein said variation calculator comprises a sampler that samples two optical rotation angles and a difference calculator that determines a difference of the two angles as the variation in the optical rotation angle.

2. The concentration measuring apparatus according to claim 1, wherein the concentration calculator calculates the concentration of the optically active substance based on a preset optical rotation coefficient of the optically active substance.

3. The concentration measuring apparatus according to claim 1, wherein the optical rotation angle modulator is a liquid crystal cell.

4. The concentration measuring apparatus according to claim 1, wherein the optical rotation angle modulator is a Faraday cell.

5. The concentration measuring apparatus according to claim 1, wherein the optical rotation angle modulator is a Pockels cell.

6. The concentration measuring apparatus according to claim 1, wherein the optical rotation angle modulator comprises a combination of a homogeneous liquid crystal cell and a $\lambda/4$ wavelength polarizer.

7. The concentration measuring apparatus according to claim 1, wherein the linearly polarized light supplier comprises:
a light source that projects light;
a light polarizer that polarizes the light to obtain linearly polarized light; and
a beam diameter adjusting lens disposed between the light source and the light polarizer, and configured to adjust a beam diameter of the light to a predetermined beam diameter.

8. The concentration measuring apparatus according to claim 1, further comprising a collecting lens that collects the light coming out of the inspection object on the light intensity detector.

9. The concentration measuring apparatus according to claim 1, wherein the optically active substance is glucose in the blood.

10. The concentration measuring apparatus according to claim 1, wherein the optically active substance is plasma protein in the blood.

11. The concentration measuring apparatus according to claim 1, wherein the optically active substance is cholesterol in the blood.

12. A concentration measuring apparatus comprising:
a linearly polarized light supplier that supplies linearly polarized light;
an optical rotation angle modulator that modulates an optical rotation angle of the linearly polarized light to obtain modulated light;
a light intensity detector that detects an intensity of light coming out of an inspection object when the modulated light is passed through the inspection object, wherein an optically active substance in the inspection object optically rotates the modulated light when the modulated light passes through the inspection object;
a variation calculator that calculates a variation in the optical rotation angle of the light coming out of the inspection object based on an angle to which the optical rotation angle modulator has modulated the linearly polarized light and the intensity of the light detected by the light intensity detector, wherein the optical rotation angle of the light coming out of the inspection object varies in response to a pulsation of a pulsing component of the inspection object; and
a concentration calculator that calculates a concentration of the optically active substance based on the variation in the optical rotation angle, wherein the variation calculator comprises:
a sampler that samples a first optical rotation angle and a second optical rotation angle from among plural optical rotation angles modulated by the optical rotation angle modulator, wherein the first optical rotation angle corresponding to an intensity detected by the light intensity detector at which an amplitude of the pulsing component is maximum, and the second optical rotation angle corresponding to an intensity detected by the light intensity detector at which an amplitude of the pulsing component is minimum; and a difference calculator that calculates a difference between the first optical rotation angle and the second optical rotation angle as the variation in the optical rotation angle.

13. The concentration measuring apparatus according to claim 12, wherein
a said sampler samples a first optical rotation angle and a second optical rotation angle from among a plurality of optical rotation angles modulated by the optical rotation angle modulator within a pulsing period for the pulsing component to pulse.

14. A concentration measuring apparatus comprising:
a linearly polarized light supplier that supplies linearly polarized light;
an optical rotation angle modulator that modulates an optical rotation angle of the linearly polarized light to obtain modulated light;
a light intensity detector that detects an intensity of light coming out of an inspection object when the modulated light is passed through the inspection object, wherein an optically active substance in the inspection object optically rotates the modulated light when the modulated light passes through the inspection object;
a variation calculator that calculates a variation in the optical rotation angle of the light coming out of the inspection object based on an angle to which the optical rotation angle modulator has modulated the linearly polarized light and the intensity of the light detected by the light intensity detector, wherein the optical rotation angle of the light coming out of the inspection object varies in response to a pulsation of a pulsing component of the inspection object; and
a concentration calculator that calculates a concentration of the optically active substance based on the variation in the optical rotation angle, wherein
the optical rotation angle modulator comprises a combination of a homogeneous liquid crystal cell and a first $\lambda/4$ wavelength polarizer, and a second $\lambda/4$ wavelength polarizer,
the combination is configured to modulate the linearly polarized light and emit the optical rotation angle modulated linearly polarized light to the inspection object, and
the second $\lambda/4$ wavelength polarizer has an optical axis perpendicular to an optical axis of the first $\lambda/4$ wavelength polarizer.

15. A concentration measuring method comprising:
supplying linearly polarized light;
modulating an optical rotation angle of the linearly polarized light to obtain modulated light;
passing the modulated light through an inspection object containing an optically active substance;
detecting an intensity of light coming out of an inspection object, wherein the optically active substance in the inspection object optically rotates the modulated light when the modulated light passes through the inspection object;
calculating a variation in the optical rotation angle of the light coming out of the inspection object based on the optical rotation angle to which the linearly polarized light was modulated and the intensity of the light detected, wherein the optical rotation angle of the light coming out of the inspection object varies in response to a pulsation of a pulsing component of the inspection object;

calculating a concentration of the optically active substance based on the variation in the optical rotation angle, and
providing an output related to the calculated concentration of the optically active substance,
wherein calculating a variation comprises sampling of two optical rotation angles and determining a difference of the two angles as the variation in the optical rotation angle.

16. The concentration measuring method according to claim 15, wherein the concentration of the optically active substance is calculated based on a preset optical rotation coefficient of the optically active substance.

17. A concentration measuring method comprising:
supplying linearly polarized light;
modulating an optical rotation angle of the linearly polarized light to obtain modulated light;
passing the modulated light through an inspection object containing an optically active substance;
detecting an intensity of light coming out of an inspection object, wherein the optically active substance in the inspection object optically rotates the modulated light when the modulated light passes through the inspection object;
calculating a variation in the optical rotation angle of the light coming out of the inspection object based on the optical rotation angle to which the linearly polarized light was modulated and the intensity of the light detected, wherein the optical rotation angle of the light coming out of the inspection object varies in response to a pulsation of a pulsing component of the inspection object; and
calculating a concentration of the optically active substance based on the variation in the optical rotation angle, and
providing an output related to the calculated concentration of the optically active substance, wherein the calculating a variation step comprises:
sampling a first optical rotation angle and a second optical rotation angle among a plurality of optical rotation angles modulated by the optical rotation angle modulator, wherein the first optical rotation angle corresponding to an intensity detected at the detecting an intensity step at which an amplitude of the pulsing component is maximum, and the second optical rotation angle corresponding to an intensity detected at the detecting an intensity at which an amplitude of the pulsing component is minimum; and
calculating a difference between the first optical rotation angle and the second optical rotation angle as the variation in the optical rotation angle.

18. The concentration measuring method according to claim 17, wherein the sampling step comprises:
sampling a first optical rotation angle and a second optical rotation angle among a plurality of optical rotation angles modulated by the optical rotation angle modulator within a pulsing period for the pulsing component to pulse.

* * * * *